(12) United States Patent
Whitman et al.

(10) Patent No.: US 8,121,682 B2
(45) Date of Patent: Feb. 21, 2012

(54) COMBINED HEMODYNAMIC AND EGM-BASED ARRHYTHMIA DETECTION

(75) Inventors: Teresa A. Whitman, Dayton, MN (US); Arun Kumar, Blaine, MN (US); Karen J. Kleckner, New Brighton, MN (US); Jeffrey M. Gillberg, Coon Rapids, MN (US); Troy E. Jackson, New Brighton, MN (US); Maneesh Shrivastav, Blaine, MN (US); Mark L. Brown, North Oaks, MN (US)

(73) Assignee: Medtronic, Inc., Minneapolis, MN (US)

( * ) Notice: Subject to any disclaimer, the term of this patent is extended or adjusted under 35 U.S.C. 154(b) by 206 days.

(21) Appl. No.: 12/729,454

(22) Filed: Mar. 23, 2010

(65) Prior Publication Data

US 2010/0241182 A1    Sep. 23, 2010

Related U.S. Application Data

(60) Provisional application No. 61/162,535, filed on Mar. 23, 2009.

(51) Int. Cl.
*A61N 1/00* (2006.01)
(52) U.S. Cl. ......................................................... 607/5
(58) Field of Classification Search ........................ 607/5
See application file for complete search history.

(56) References Cited

U.S. PATENT DOCUMENTS

| | | | |
|---|---|---|---|
| 4,774,950 A | 10/1988 | Cohen | |
| 5,163,429 A | 11/1992 | Cohen | |
| 5,342,404 A | 8/1994 | Alt et al. | |
| 6,752,765 B1 * | 6/2004 | Jensen et al. | 600/536 |
| 6,873,870 B2 | 3/2005 | Ferek-Petric | |
| 6,915,162 B2 | 7/2005 | Noren et al. | |
| 7,233,822 B2 | 6/2007 | Hettrick et al. | |
| 2005/0154421 A1 | 7/2005 | Ousdigian | |
| 2006/0116590 A1 | 6/2006 | Fayram et al. | |
| 2007/0239215 A1 | 10/2007 | Bhunia et al. | |
| 2008/0288013 A1 | 11/2008 | Schecter | |
| 2009/0254137 A1 | 10/2009 | Salo et al. | |
| 2009/0299429 A1 | 12/2009 | Mayotte et al. | |

FOREIGN PATENT DOCUMENTS

WO    2004091719    10/2004

OTHER PUBLICATIONS (PCT/US2010/028213) PCT Notification of Transmittal of the International Search Report and the Written Opinion of the International Searching Authority, Jul. 2, 2010, 11 pages.
Petrucci E. et al., Right Ventricular Pressure and VTs Tolerance, J Cardiovasc Electrophysiol, vol. 20, pp. 299-306, Mar. 2009.

* cited by examiner

*Primary Examiner* — George Manuel
(74) *Attorney, Agent, or Firm* — Michael C. Soldner

(57) ABSTRACT

A medical device and associated method for detecting arrhythmias that includes sensing cardiac electrical signals and cardiac hemodynamic signals, determining a long-term baseline hemodynamic measurement in response to a plurality of the sensed cardiac hemodynaic signals, detecting a period of increased metabolic demand in response to the sensed cardiac electrical signals, determining a sinus tachycardia baseline hemodynamic measurement in response sensing of cardiac hemodynamic signals during the detected period of increased metabolic demand, and detecting the arrhythmia and delivering therapy in response to one of only the sensed cardiac electrical signals and the sensed cardiac electrical signals in combination with one or both of the determined long-term baseline hemodynamic measurement and the sinus tachycardia baseline hemodynamic measurement.

22 Claims, 8 Drawing Sheets

COMBINED HEMODYNAMIC AND EGM-BASED ARRHYTHMIA DETECTION

RELATED PRIORITY APPLICATION

The present application claims priority and other benefits from U.S. Provisional Patent Application Ser. No. 61/162,535, filed Mar. 23, 2009, entitled "USE OF HEMODYNAMICS AS AN ADJUNCT TO ICD TACHYCARDIA EGM-BASED DISCRIMINATION", incorporated herein by reference in it's entirety.

TECHNICAL FIELD

The disclosure relates generally to implantable medical devices and, in particular, to a method and apparatus for detecting and treating arrhythmias.

BACKGROUND

Implantable cardioverter defibrillators (ICDs) are configured to evaluate intracardiac electrogram (EGM) signals for detecting cardiac arrhythmias. Typically a fast rhythm is detected based on EGM sensed event intervals, e.g. RR intervals. However, not all fast heart rates meeting arrhythmia detection criteria are lethal arrhythmias that require a cardioversion or defibrillation shock. For example, a fast ventricular rate may be sinus tachycardia in response to physical exertion. In other cases, oversensing of cardiac events may result in an overestimate of the actual heart rate, which can cause false tachycardia detections. While it is desirable to quickly detect and treat potentially lethal arrhythmias, such as ventricular fibrillation, it is also desirable to avoid painful defibrillation shocks when such shocks are unnecessary. A need remains for improved methods for detecting arrhythmias and discriminating between potentially lethal arrhythmias associated with hemodynamic collapse and non-lethal, fast rhythms that do not require immediate therapy.

DETAILED DESCRIPTION

Figure 1:
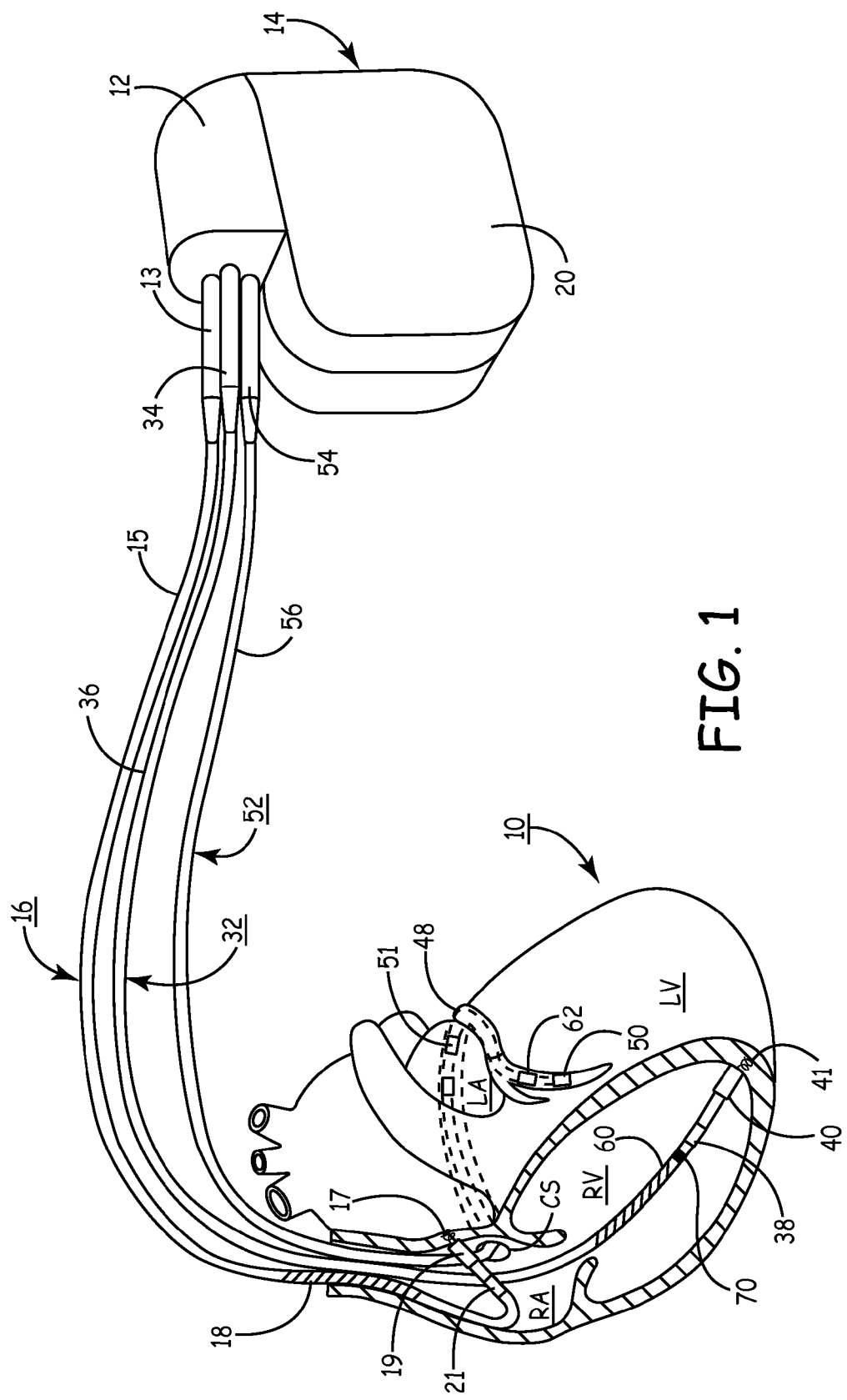
FIG. 1 depicts an implantable, cardiac stimulation device embodied as an implantable cardioverter defibrillator (ICD).

In the following description, references are made to illustrative embodiments. It is understood that other embodiments may be utilized without departing from the scope of the invention. For purposes of clarity, the same reference numbers are used in the drawings to identify similar elements. As used herein, the term "module" refers to an application specific integrated circuit (ASIC), an electronic circuit, a processor (shared, dedicated, or group) and memory that execute one or more software or firmware programs, a combinational logic circuit, or other suitable components that provide the described functionality.

FIG. 1 depicts an implantable, cardiac stimulation device embodied as an implantable cardioverter defibrillator (ICD) 14, in which methods described herein may be implemented. Various embodiments of the invention may be implemented in numerous types of implantable medical devices capable of sensing cardiac signals, such as pacemakers, ECG monitors, and hemodynamic monitors. ICD 14 is provided for sensing intrinsic heart activity and delivering cardiac stimulation pulses in the form of pacing, cardioversion or defibrillation therapy, as appropriate, to one or more heart chambers.

ICD 14 is shown in communication with a patient's heart 10 by way of three leads 16, 32 and 52. The heart 10 is shown in a partially cut-away view illustrating the upper heart chambers, the right atrium (RA) and left atrium (LA), and the lower heart chambers, the right ventricle (RV) and left ventricle (LV), and the coronary sinus (CS) in the right atrium leading into the great cardiac vein 48, which branches to form inferior cardiac veins. Leads 16, 32 and 52 connect ICD 14 with the RA, the RV and the LV, respectively. Each lead has at least one electrical conductor and pace/sense electrode. A remote indifferent can electrode is formed as part of the outer surface of the ICD housing 20. The pace/sense electrodes and the remote indifferent can electrode can be selectively employed to provide a number of unipolar and bipolar pace/sense electrode combinations for pacing and sensing functions.

RA lead 16 is passed through a vein into the RA chamber and may be attached at its distal end to the RA wall using a fixation member 17. RA lead 16 is formed with a connector 13 fitting into a connector bore of ICD connector block 12 for electrically coupling RA tip electrode 19 and RA ring electrode 21 to ICD circuitry housed within housing 20 via insulated conductors extending within lead body 15. RA tip electrode 19 and RA ring electrode 21 may be used in a bipolar fashion, or in a unipolar fashion with ICD housing 20, for achieving RA stimulation and sensing of RA EGM signals. RA lead 16 is also provided with a coil electrode 18 that may be used for delivering high voltage cardioversion/defibrillation pulses to heart 10 in response to the detection of tachycardia or fibrillation.

RV lead 32 is passed through the RA into the RV where its distal end, carrying RV tip electrode 40 and RV ring electrode 38 provided for stimulation in the RV and sensing of RV EGM signals, is fixed in place in the RV apex by a distal fixation member 41. RV lead 32 also carries a high-voltage coil electrode 60 for use in cardioverting and defibrillating heart 10. RV lead 32 is formed with a connector 34 fitting into a corresponding connector bore of ICD connector block 12. Connector 34 is coupled to electrically insulated conductors within lead body 36 and connected with distal tip electrode 40, ring electrode 38 and coil electrode 60.

RV lead 32 additionally carries a pressure sensor 70 for sensing RV pressure signals. Pressure sensor 70 is coupled to ICD 14 via a conductor extending through lead body 36. In alternative embodiments, any of leads 16, 32 and 52 may carry a physiological sensor producing a signal responsive to the hemodynamic function of the heart 10. As will be described in detail herein, a hemodynamic signal is used in conjunction with a sensed EGM signal for detecting and discriminating arrhythmias.

Coronary sinus lead 52 is passed through the RA, into the CS and further into a cardiac vein 48 to extend the distal LV tip electrode 50 and ring electrode 62 alongside the LV chamber to achieve LV stimulation and sensing of LV EGM signals. The LV CS lead 52 is coupled at the proximal end connector 54 into a bore of ICD connector block 12 to provide electrical coupling of conductors extending from electrodes 50 and 62 within lead body 56 to ICD internal circuitry. In some embodiments, LV CS lead 52 could bear a proximal LA pace/sense electrode 51 positioned along CS lead body 56 such that it is disposed proximate the LA for use in stimulating the LA and/or sensing LA EGM signals.

In addition to the lead-mounted electrodes, ICD 14 may include one or more subcutaneous cardiac sensing electrodes (not shown) formed as uninsulated portions of the ICD housing 20 or included in the connector block 12. While a particular ICD system with associated leads and electrodes is illustrated in FIG. 1, numerous implantable cardiac monitoring, pacemaker and ICD system configurations are possible, which may include one or more leads deployed in transvenous, subcutaneous, or epicardial locations. The lead and electrode arrangements will depend on the particular application. Methods described herein which combined hemodynamic and EGM signal analysis in arrhythmia detection algorithms may also be implemented in subcutaneous cardiac monitor, pacemaker or ICD systems in which electrodes are formed as a part of the device housing and/or carried by subcutaneous leads.

ICD 14 is shown as a multi-chamber device capable of sensing and stimulation in three or all four heart chambers. It is understood that ICD 14 may be modified to operate as a single chamber device or dual chamber device. In the illustrative embodiments, described herein, methods for arrhythmia detection are described in which ventricular EGM and pressure signals are sensed and used for detecting arrhythmias and making therapy delivery decisions. It is contemplated that the methods described, however, may be used in dual chamber, triple chamber or all four chamber applications in which both ventricular and atrial EGM signals are available.

Figure 2:
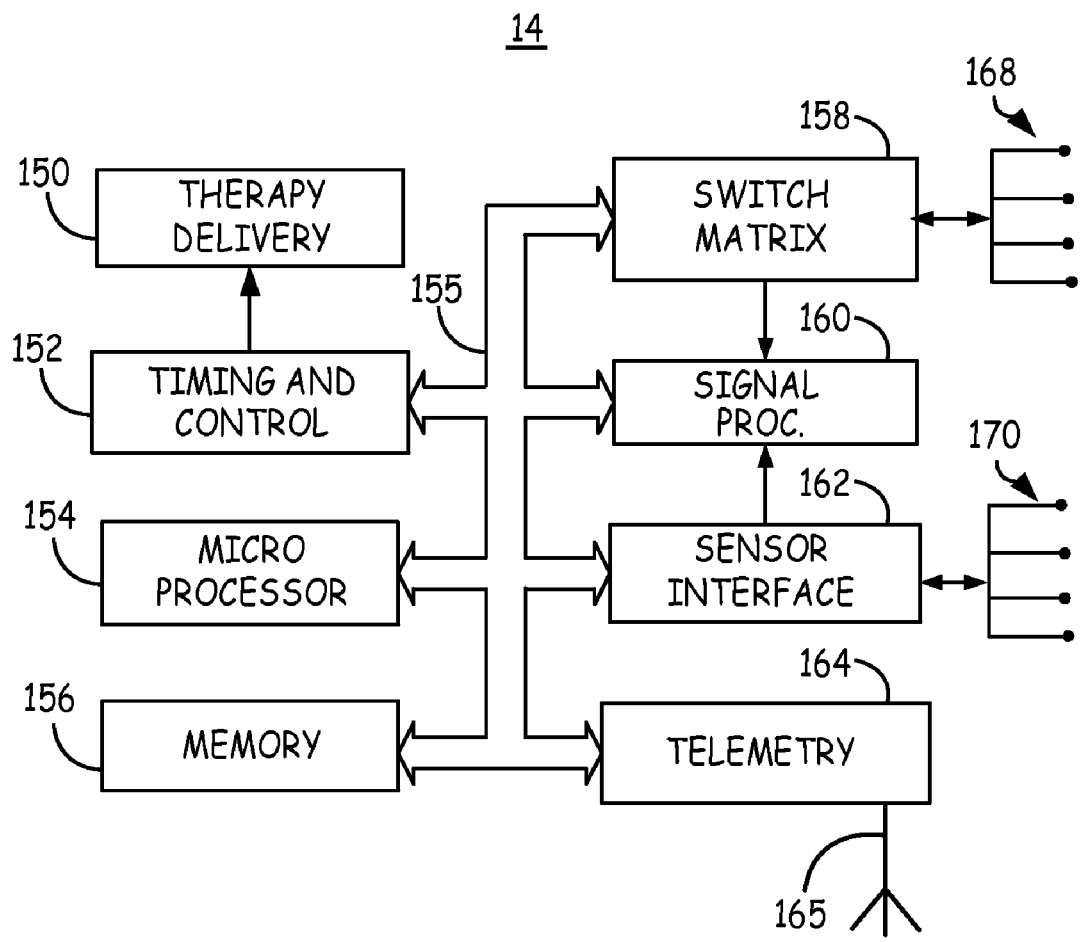
FIG. 2 is a functional block diagram of the ICD shown in FIG. 1 according to one embodiment.

FIG. 2 is a functional block diagram of the ICD 14 shown in FIG. 1 according to one embodiment. ICD 14 generally includes timing and control circuitry 152 and an operating system that may employ microprocessor 154 or a digital state machine for timing sensing and therapy delivery functions in accordance with a programmed operating mode. Microprocessor 154 and associated memory 156 are coupled to the various components of ICD 14 via a data/address bus 155. ICD 14 includes therapy delivery module 150 for delivering electrical stimulation therapies, such as cardiac pacing therapies and arrhythmia therapies including cardioversion/defibrillation shocks and anti-tachycardia pacing (ATP), under the control of timing and control 152. Therapy delivery module 150 is typically coupled to two or more electrodes 168 via an optional switch matrix 158. Switch matrix 158 is used for selecting which electrodes and corresponding polarities are used for delivering electrical stimulation pulses.

Cardiac electrical signals are sensed for use in determining when an electrical stimulation therapy is needed and in controlling a stimulation mode and the timing of stimulation pulses. Electrodes 168 used for sensing are coupled to signal processing circuitry 160. Signal processor 160 includes sense amplifiers and may include other signal conditioning circuitry and an analog-to-digital converter. Electrical signals may then be used by microprocessor 154 or other control circuitry for detecting physiological events, such as detecting and discriminating cardiac arrhythmias. Signal processing circuitry 160 may include event detection circuitry generally corresponding to R-wave detection circuitry as disclosed in U.S. Pat. No. 5,117,824 (Keimel, et al.), hereby incorporated herein by reference in its entirety.

Arrhythmia detection algorithms may be implemented for detecting tachycardia and fibrillation and for discriminating between ventricular arrhythmias and supraventricular arrhythmias (SVTs). For example, ventricular tachycardia (VT), fast ventricular tachycardia (FVT) and ventricular fibrillation (VF) may be detected using sensed EGM signals. Ventricular event intervals (R-R intervals) sensed from the EGM signals are commonly used for detecting ventricular arrhythmias. Additional information obtained such as R-wave morphology, slew rate, other event intervals (P-R intervals) or other sensor signal information may be used in detecting, confirming or discriminating an arrhythmia. Reference is made to U.S. Pat. Nos. 5,354,316 (Keimel); 5,545,186 (Olson et al.); and U.S. Pat. No. 6,393,316 (Gillberg et al.) for examples of arrhythmia detection and discrimination using EGM signals, all of which patents are incorporated herein by reference in their entirety.

In one detection scheme, programmable detection interval ranges designate the range of sensed event intervals indicative of a tachycardia and may be defined separately for detecting VT, FVT and VF. Sensed event intervals falling into defined detection interval ranges are counted to provide a count of tachycardia or fibrillation intervals. A programmable number of intervals to detect (NID) defines the number of tachycardia/fibrillation intervals occurring consecutively or out of a given number of preceding event intervals that are required to detect tachycardia or fibrillation. A separately programmed NID may be defined for detecting VT, FVT, and VF. In addition to the interval ranges and NID criteria, rapid onset criterion and rate stability criterion may also be defined for use in arrhythmia detection schemes. Furthermore, a combined count of tachycardia and fibrillation intervals may be compared to a combined count threshold and, according to predefined criteria, used in detecting fibrillation or slow or fast tachycardia.

In addition to event interval information, the morphology of the EGM signal may be used in discriminating heart rhythms, for example as described in the above-incorporated '316 Gillberg patent. According to one embodiment of the invention, digitized EGM signals are provided to microprocessor 154 for waveform analysis according to an implemented morphology or template matching algorithm. Morphology analysis may be used in conjunction with event interval analysis to improve the sensitivity and specificity of arrhythmia detection methods.

ICD 14 is additionally coupled to one or more physiological sensors 170. Physiological sensors 170 include at least one sensor responsive to cardiac hemodynamic function. In one embodiment, sensors 170 include a pressure sensor adapted for placement within a ventricle of the heart as shown in FIG. 1 for providing an intraventricular pressure signal. In other embodiments, sensors 170 may include a motion sensor such as an accelerometer, a flow sensor, blood chemistry sensors such as an oxygen saturation sensor, activity sensors, an acoustical sensor, or other physiological sensors. Physiological sensors may be carried by any lead extending from ICD 14, incorporated in or on the ICD housing or may be embodied as leadless sensors implanted in the body and in telemetric communication with the ICD or another device.

As will be described in detail herein, a hemodynamic signal is acquired from physiological sensors 170 for use in arrhythmia detection and therapy delivery decisions. As used herein, the term "hemodynamic signal" refers generally to a signal measuring effects of the mechanical pumping function of the heart. A hemodynamic signal may be, but not necessarily limited to, a motion signal, a pressure signal, a flow signal, or an acoustical signal. Accordingly, hemodynamic sensors include sensors generating a signal corresponding to heart or vessel wall motion, arterial or intracardiac blood pressure, blood flow, or heart sounds. The hemodynamic signal is used to verify an arrhythmia episode detection made using cardiac electrical signals and for making appropriate therapy delivery decisions based on the hemodynamic status of the patient at the time of an arrhythmia episode detection.

Signals from sensors 170 are received by a sensor interface 162 which provides sensor signals to signal processing circuitry 160. Sensor signals are used by microprocessor 154 for detecting physiological events or conditions. For example, ICD 14 may monitor heart wall motion, blood pressure, blood chemistry, respiration, or patient activity. Monitored signals may be used for sensing the need for delivering or adjusting a therapy under control of the operating system. Monitored sensor signals may be analyzed to obtain diagnostic or prognostic data stored by ICD and made available to a clinician.

The ICD operating system includes associated memory 156 for storing a variety of programmed-in operating mode and parameter values that are used by microprocessor 154. Algorithms for detecting arrhythmias, delivering arrhythmia therapy, and associated parameter values may be stored in memory 156. The memory 156 may also be used for storing data compiled from sensed EGM and physiological signals and/or relating to device operating history for telemetry out on receipt of a retrieval or interrogation instruction.

In response to an arrhythmia detection, a programmed arrhythmia therapy is delivered by therapy delivery module 150 under the control of timing and control 152. A description of high-voltage output circuitry and control of high-voltage shock pulse delivery is provided, for example, in the above-incorporated '186 Olson patent. Typically, a tiered menu of arrhythmia therapies are programmed into the device ahead of time by the physician and stored in memory 156. For example, on initial detection of VT, an anti-tachycardia pacing therapy may be delivered. On redetection of tachycardia, a more aggressive anti-tachycardia pacing therapy may be scheduled. If repeated attempts at anti-tachycardia pacing therapies fail, a high voltage cardioversion pulse may be selected to more aggressively treat the detected arrhythmia. Therapies for tachycardia termination may vary with the rate of the detected tachycardia, with the therapies increasing in aggressiveness as the rate of the detected tachycardia increases. For example, fewer attempts at anti-tachycardia pacing may be undertaken prior to delivery of cardioversion pulses if the rate of the detected tachycardia is above a preset threshold.

In the event that fibrillation is identified, which may be atrial fibrillation or ventricular fibrillation, high frequency burst stimulation may be employed as the initial attempted therapy. Subsequent therapies may include high voltage defibrillation pulses. The defibrillation pulse energy may be increased if an initial shock pulse fails to terminate fibrillation. As will be described herein, hemodynamic signal information may be used to modify the progression of a programmed menu of tiered therapies.

ICD 14 further includes telemetry circuitry 164 and antenna 165. Programming commands or data are transmitted during uplink or downlink telemetry between ICD telemetry circuitry 164 and external telemetry circuitry included in a programmer or monitoring unit.

Figure 3:
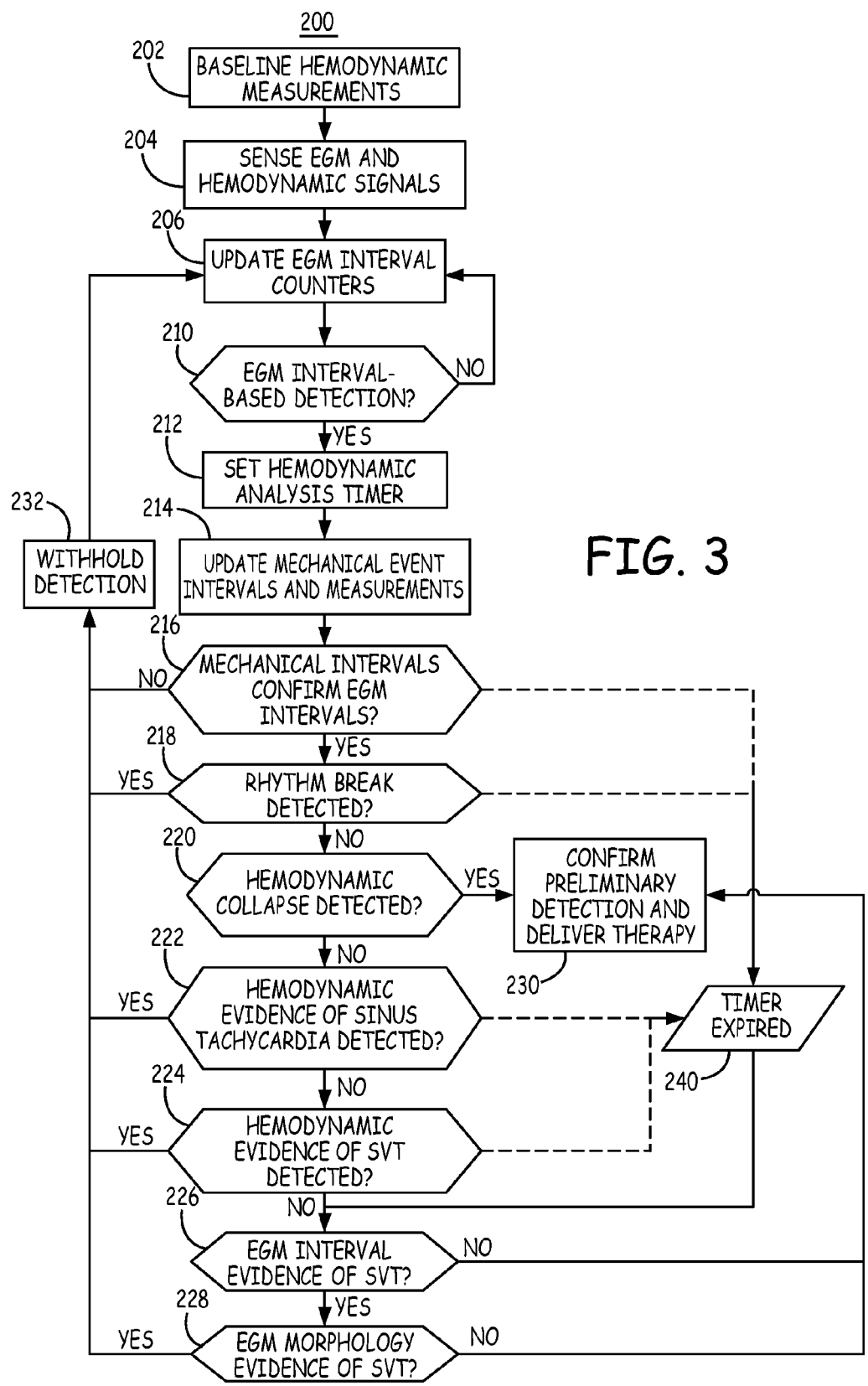
FIG. 3 is a flow chart of a method for using hemodynamic signals in an ICD for the detection of cardiac arrhythmias and in making arrhythmia therapy decisions.

FIG. 3 is a flow chart 200 of a method for using hemodynamic signals in an ICD for the detection of cardiac arrhythmias and in making arrhythmia therapy decisions. Flow chart 200 is intended to illustrate the functional operation of the device, and should not be construed as reflective of a specific form of software or hardware necessary to practice the methods described. It is believed that the particular form of software, firmware or hardware will be determined primarily by the particular system architecture employed in the device and by the particular detection and therapy delivery methodologies employed by the device. Providing software, firmware or hardware to accomplish the described functionality in the context of any modern ICD, given the disclosure herein, is within the abilities of one of skill in the art.

Methods described in conjunction with flow charts presented herein may be implemented in a computer-readable medium that includes instructions for causing a programmable processor to carry out the methods described. A "computer-readable medium" includes but is not limited to any volatile or non-volatile media, such as a RAM, ROM, CD-ROM, NVRAM, EEPROM, flash memory, and the like. The instructions may be implemented as one or more software modules, which may be executed by themselves or in combination with other software.

At block 202, baseline hemodynamic measurements are acquired, stored and evaluated for use in arrhythmia detection. In one embodiment, at least two baseline measurements are acquired, a long-term (LT) baseline hemodynamic measurement and a sinus tachycardia (ST) baseline measurement. The LT and ST baseline measurements will be compared to qualification criteria to determine if the hemodynamic baseline measurements are useful and reliable for arrhythmia detection and therapy delivery decisions. Computation and qualification of baseline measurements will be described in greater detail below in conjunction with FIG. 4.

At block 204, cardiac EGM signals and a hemodynamic signal are sensed for rhythm monitoring. In the illustrative embodiments described herein, the hemodynamic signal relied upon for arrhythmia detection and therapy delivery decision-making is an RV pressure signal. However, it is recognized that the methods described herein may be adapted to use other blood pressure signals, flow signals, motion signals, heart sound signals or any other available hemodynamic signal responsive to cardiac mechanical function.

At block 206, electrical event interval counters are updated as cardiac electrical events, i.e., R-waves (and P-waves in dual chamber devices), are sensed. Electrical event interval counters track the number of intervals meeting arrhythmia detection criteria. More specifically, in a single chamber ventricular ICD, for example, R-waves are sensed and RR intervals are measured. The RR intervals are compared to stored interval ranges for arrhythmia detection zones. As described previously, detection interval ranges are defined for different rate zones, e.g., VT, fast VT and VF rate zones. A number of intervals to detect (NID) are additionally defined for each rate zone. The detection interval range and the NID for each rate zone are typically programmable. As RR intervals falling in an arrhythmia detection interval range are detected, a corresponding interval counter (VT, FVT, VF or combined count) is updated at block 206.

If any of the interval counters reach the NID criteria, a preliminary, i.e., not yet confirmed, arrhythmia detection is made at block 210 based only on the EGM interval criteria. When a preliminary arrhythmia detection is made, a hemodynamic analysis timer is optionally set at block 212. During the operation of method 200, one or more timers may be set to control the amount of time allowed for an arrhythmia detection to be withheld based on hemodynamic signal analysis. A hemodynamic analysis timer may be set to different intervals depending on the detected heart rate. For example, a hemodynamic analysis timer may be set to a shorter interval when a preliminary VF detection is made at block 206, and the timer may be set to a relatively longer interval when VT is preliminarily detected.

Furthermore, a hemodynamic analysis timer may be set to different intervals depending on whether the detection made at block 206 is the initial, i.e., first confirmed, detection of an arrhythmia episode or redetection of the arrhythmia episode. Accordingly, a hemodynamic analysis timer may be set to at least 4 different time intervals corresponding to at least four different conditions occurring at block 210 based on cycle length conditions (for example VT detection range or VF detection range) and initial detection and redetection conditions. In an alternative embodiment, separate timers may be set for controlling the amount of time allowed to withhold an arrhythmia detection based on the hemodynamic analyses performed at each of the respective blocks 216, 218, 222, and 224. It is recognized that a hemodynamic analysis timer limiting the time an arrhythmia detection is withheld due to hemodynamic signal information is optional and when implemented may be programmed to be disabled or "off".

At block 214, mechanical event interval and mechanical event measurements are acquired or updated for use in hemodynamic analyses performed at blocks 216 through 224. Mechanical event intervals and hemodynamic measurements are obtained from the sensed hemodynamic signal.

The hemodynamic signal may be recorded without performing signal analysis until a preliminary arrhythmia detection is made. Alternatively, hemodynamic event interval and event measurements can be made from a hemodynamic signal on a continuous basis so that hemodynamic data is immediately available upon preliminary arrhythmia detection. Such data may then be evaluated retrospectively when a preliminary arrhythmia detection is made. Various measurements of hemodynamic events and event intervals are made at block 214 for use in comparing to baseline measurements and to the detected electrical event intervals, respectively, as will be further described herein.

At block 216, mechanical event intervals are used to confirm the electrical event intervals measured from the EGM signal leading to the preliminary arrhythmia detection made at block 210. One method for using mechanical event intervals to confirm the presence of a fast electrical event rate is described below in conjunction with FIG. 5.

At block 218, mechanical event measurements are used to detect a break in the arrhythmia episode. In other words, measurements of mechanical events are used to detect a non-sustained arrhythmia. Good hemodynamic function associated with an RR interval that is longer than a maximum arrhythmia detection interval and occurring during the preliminarily detected arrhythmia episode is evidence of a non-sustained arrhythmia. One method for detecting a break in the arrhythmia episode is described below in conjunction with FIG. 6.

At block 220, mechanical event measurements are used to discriminate between a potentially lethal arrhythmia, associated with hemodynamic collapse, and non-lethal arrhythmias, in which hemodynamic function is expected to be adequate to sustain consciousness. If hemodynamic collapse is detected, the preliminary arrhythmia detection is confirmed and programmed therapies are immediately delivered according to a menu of tiered therapies at block 224. Alternatively, a programmed menu of tiered therapy may be overridden in response to detecting hemodynamic collapse and a more aggressive therapy, e.g., a high voltage shock therapy, may be immediately delivered.

If hemodynamic collapse is not detected at block 220, but hemodynamic data confirms the EGM-based arrhythmia detection up to this point (EGM intervals confirmed at block 216 and no rhythm break detected at block 218), additional hemodynamic measurement rules are applied for use in making an appropriate therapy delivery decision. At block 222, hemodynamic criteria are applied to the mechanical event measurements for discriminating between pathologic VT and sinus tachycardia.

If the preliminary detected episode is determined to be sinus tachycardia based on the hemodynamic criteria, arrhythmia detection is withheld at block 232. Therapy delivery is not initiated. Method 200 returns to block 206 to continue monitoring the electrical event intervals and update EGM interval counters. Mechanical event intervals and measurements will be updated upon redetection of the arrhythmia episode. Mechanical event data may be logged in memory with other episode data such that it is available for later review by a clinician.

At block 224, hemodynamic criteria are applied to the mechanical event measurements to discriminate between ventricular and supraventricular arrhythmias. If the detected episode is determined to be SVT based on hemodynamic criteria being satisfied, the preliminary ventricular arrhythmia detection is withheld at block 232, and ventricular therapy delivery is not initiated. Method 200 returns to block 204 to continue monitoring electrical event intervals and update the mechanical event measurements as needed.

If the hemodynamic measurements do not meet sinus tachycardia or SVT rules applied at blocks 222 and 224, additional analysis of the EGM signals may be performed at blocks 226 and 228 to discriminate or confirm the detected arrhythmia episode. For example, at block 226, measured RR intervals may be compared to SVT interval criteria for discriminating between VT and SVT. In one embodiment, if a median RR interval is determined to be shorter than an SVT RR interval limit at block 226, the preliminary VT, FVT or VF initially made at block 206 is confirmed. Method 200 advances to block 230 to deliver arrhythmia therapy according to a programmed menu of tiered therapy.

If SVT criteria applied to the RR interval measurements at block 226 are met, morphological analysis of the EGM signal is performed at block 228. For example, wavelet analysis may be performed as generally described in the above-referenced Gillberg patent. Based on the wavelet or other morphological analysis of the EGM signal waveform, block 228, the preliminary ventricular arrhythmia detection made at block 206 may be either confirmed or withheld. If confirmed, the appropriate VT, FVT or VF therapy is delivered at block 230 according to programmed therapies. If withheld, method 200 returns to block 206 to continue updating electrical event interval counters and mechanical event intervals and measurements.

If the preliminary arrhythmia episode is redetected at block 210 after withholding an arrhythmia detection due to any of the hemodynamic analyses at blocks 216, 218, 222, and 224, any or all of the hemodynamic analysis performed at those blocks may be disabled. For example, if the electrical event intervals are confirmed at block 216 based on measured mechanical event intervals following a preliminary arrhythmia detection, the analysis at block 216 may be disabled following an EGM interval-based redetection of the same arrhythmia episode. In other words, once the electrical event intervals are confirmed to not be overestimating the heart, for example due to oversensing, the mechanical event intervals are not used again to verify the electrical event intervals. Likewise, hemodynamic analysis performed at block 220 may be disabled following a preliminary arrhythmia detection and enabled to detect hemodynamic collapse following an EGM interval-based redetection of the same episode. The hemodynamic collapse detection at block 220 may also be applied only when the preliminary detection or redetection is a FVT or VF and not applied for a preliminary detection or redetection of a VT.

If the hemodynamic analysis timer expires (block 240), method 200 may immediately advance to perform additional EGM signal analysis at block 226 and/or block 228 and skip additional hemodynamic analysis. In one embodiment, if the timer expires at block 240, the hemodynamic analysis is abandoned and wavelet analysis is immediately performed at block 228. If the wavelet analysis results in a withhold detection decision at block 232, then the hemodynamic analysis timer may be reset at block 214.

The hemodynamic analysis timer may also be reset if EGM interval(s) fall outside the arrhythmia detection zones or NID criteria are no longer being met. In one embodiment, the hemodynamic analysis timer is not reset at block 212 when the withhold detection decision at block 232 is arrived at through any hemodynamic analysis block 216, 218, 222, or 224. In this way, a prolonged withholding of arrhythmia detection and therapy delivery does not occur based on hemodynamic analysis alone. EGM analysis, for example wavelet analysis at block 228, is performed to ensure that prolonged detection and therapy withholding decisions are supported by both hemodynamic and EGM analysis and not hemodynamic analysis alone.

In other embodiments, interval-based, hemodynamic-based, and morphology-based measurements may each receive a level of confidence in confirming the presence of an arrhythmia. The arrhythmia detection may be made based on the confidence of each parameter measured. A single parameter with high confidence or the combined confidence of multiple parameters may lead to an arrhythmia detection. If no single or combined confidence lead to an arrhythmia detection, a preliminary detection based on a single parameter may be withheld until at least one of the other parameters worsens to reach a detection confirmation criteria or some additional amount of time has passed with no changes in the confidences of the single or other parameters. Thus, both hierarchical and non-hierarchical approaches to detecting an arrhythmia using multiple parameter analyses of both an EGM signal and a hemodynamic signal may be used.

Figure 4:
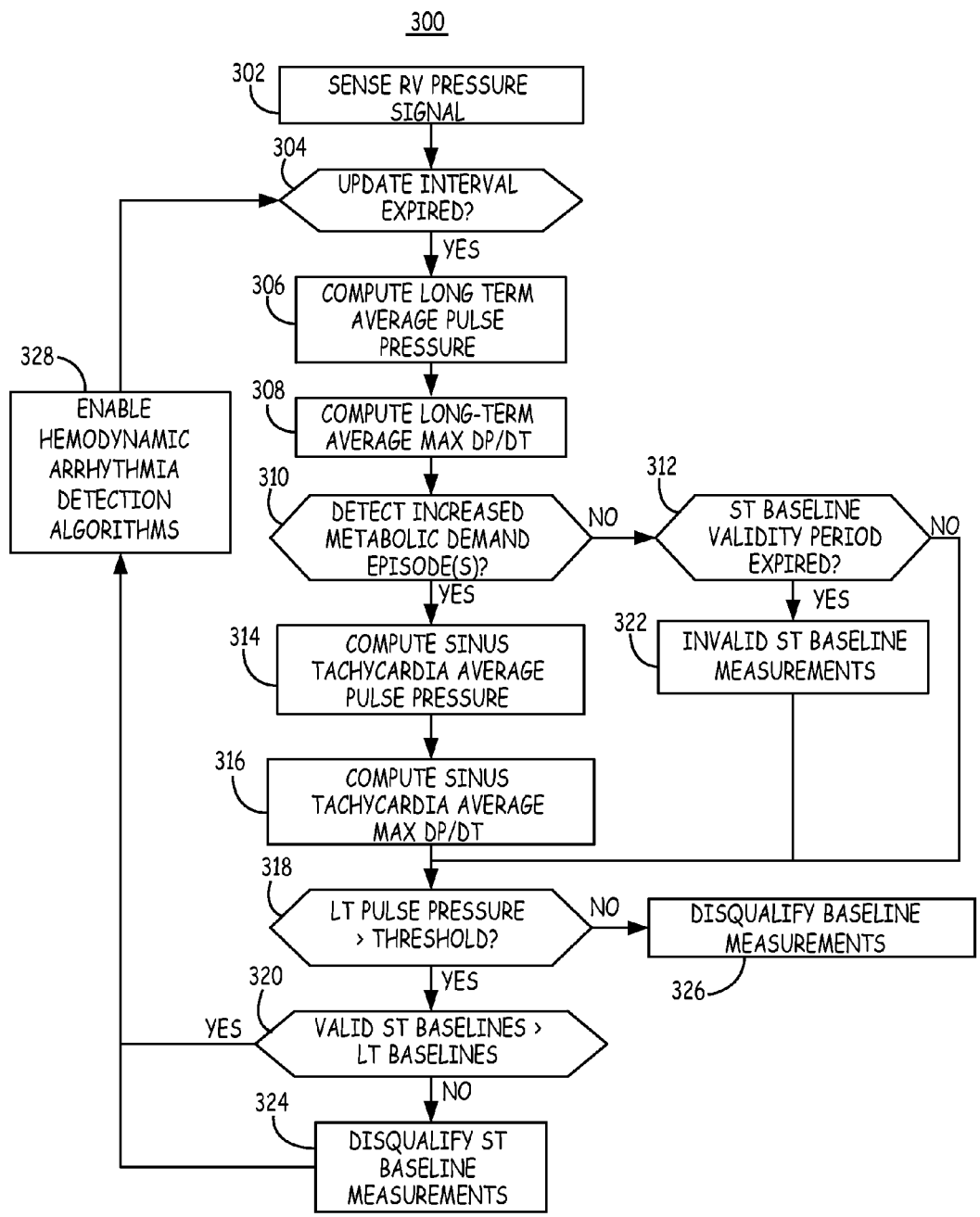
FIG. 4 is a flow chart of one method for computing and qualifying baseline hemodynamic measurements.

FIG. 4 is a flow chart of one method 300 for computing and qualifying baseline hemodynamic measurements at block 202 of method 200. As discussed previously, both long-term and sinus tachycardia baseline measurements are computed in one embodiment. The LT baseline measurements represent baseline hemodynamic function over a relatively long period of time, e.g., to encompass a range of the patient's typical activities of daily living. The ST baseline measurements correspond to a period of increased metabolic activity when the patient is in normal sinus rhythm, but at an elevated heart rate.

At block 302, an RV pressure signal is sensed continuously for computing initial baseline measurements and regularly updating the baseline measurements upon expiration of an update interval at block 304. Method 300 remains at block 304 storing hemodynamic signal data until the initial measurement period or an update interval expires.

In one embodiment, the LT baseline measurements are computed as 24-hour average values of a hemodynamic measurement. In the specific example of FIG. 4, RV pressure is continuously monitored and a 24-hour average pulse pressure is initially computed at block 306 then updated from stored data every 12 hours (or at another update interval within, at, or greater than the 24-hour period). In addition to a 24-hour average pulse pressure, a 24-hour average positive maximum dP/dt is computed at block 308. These two measurements are used as LT baseline measurements for comparison to hemodynamic measurements in response to an EGM interval-based preliminary arrhythmia detection for confirming or discriminating the arrhythmia. One detailed method for measuring pulse pressures and dP/dt on a beat-by-beat basis for use in computing baseline measurements is described below in conjunction with FIG. 5.

Other baseline measurements that may be derived from a pressure signal include a peak pressure or the area of a portion of the pressure waveform. It is recognized that if other types of hemodynamic signals are available, appropriate baseline measurements may be computed which may include a signal average, average peak-to-peak differences or absolute peak amplitudes, a peak rate of change, an integral or other measurements of the mechanical hemodynamic events.

The LT baseline measurements obtained over a relatively long period of time, for example at least one hour or one day, provide more relevant baseline measures than hemodynamic measurements obtained in the seconds or minutes just prior to a preliminary arrhythmia episode detection. Since hemodynamic function may already be altered due to changes in autonomic tone or other physiological changes leading up to an arrhythmia, hemodynamic measurements taken in the minutes or seconds before an arrhythmia detection may not accurately represent the patient's normal hemodynamic baseline function. The LT baseline measurements averaged over several hours and a range of patient activity are less susceptible to noise and effects of beat-to-beat variability, which can be observed in hemodynamic signals such as a right ventricular pressure signal.

At block 310, an increased metabolic demand is detected. In various embodiments, an increased metabolic demand may be detected as a confirmed episode of sinus tachycardia, an elevated heart rate that is above a resting rate but not yet meeting a tachycardia rate, elevated activity detected using an activity sensor, increased respiration, or any combination thereof. In one embodiment, increased metabolic demand is detected as a heart rate that is in the range of approximately 90 to approximately 110 beats per minute. In other embodiments, increased demand may be defined as a percentage or fixed interval above a patient's measured resting heart rate.

ST baseline measurements of average pulse pressure and average maximum dP/dt are computed at blocks 314 and 316 from selected sampling intervals of the monitored RV pressure signal corresponding to an interval of time in which the average heart rate is at a predefined elevated level (or when another measure of increased metabolic demand is detected). The sampling intervals may be identified as time intervals greater than a predefined minimum time interval, e.g. at least 30 seconds, during which the average heart rate is within a predetermined range, such as 90 to 110 beats per minute. In general, the RV pressure signal data is sampled during intervals in which the patient is believed to be experiencing sinus rhythm under increased metabolic demand conditions such that an expected increased hemodynamic response can be measured. The hemodynamic function measured under increased metabolic demand can be used to discriminate sinus tachycardia from pathological forms of tachycardia.

The ST baseline may be updated at the same update interval, e.g. every 12 hours, as the LT baseline, or another update interval, or each time a sampling interval is identified. The sampling intervals used for computing the ST baseline measurements may be selected from a longer period of time than the update interval. For example, all sampling intervals meeting the sampling criteria occurring during the past 24 hours may be used to update the ST baseline measurements every 12 hours. At decision block 310, method 300 determines if a minimum number of data points are available from sampling intervals meeting the increased metabolic demand detection criteria during the past 24 hour period or other defined sampling period. If not, the ST baseline measurements are not updated.

An ST baseline measurement may be considered valid for use in an arrhythmia detection algorithm for a predefined validity period, for example for 2 days, 3 days or longer. If the ST baseline measurement is not updated before the validity period expires, as determined at block 312, the ST baseline measurements are considered expired or invalid for use in arrhythmia detection and therapy delivery decision-making at block 322. As will be described below, the ST baseline measurements are used for discriminating between VT, SVT and sinus tachycardia. As such, these hemodynamic-based discrimination steps in method 200 may be disabled when an ST baseline measurement is expired. The LT baseline measurements, if qualified, may still be used for detecting hemodynamic collapse and confirming a preliminary arrhythmia detection and may be used in arrhythmia discrimination methods.

In alternative embodiments, an ST baseline may be set as a function of the LT baseline, for example a multiple or percentage greater than the LT baseline. The ST baseline is used to discriminate sinus tachycardia from a pathologic tachycardia. The ventricular pulse pressure and maximum dP/dt during sinus tachycardia are expected to exceed LT baseline measurements of these variables in a patient having enough cardiac reserve to produce a hemodynamic response to increased metabolic demand.

At blocks 318 and 320, comparative analysis of the measured baselines is performed to determine if the baseline measurements qualify for use in arrhythmia detection and therapy delivery decision-making. It is recognized that, during the computation of the baseline measurements at blocks 306, 308, 314 and 316, outlier or artifact values of the measured hemodynamic signal may be discarded when determining average or median values of the baseline measurements. Numerous methods for artifact rejection may be employed. However, once a baseline measurement is obtained, the magnitude of the hemodynamic measurement is examined to determine if reliable distinction between normal hemodynamic function and hemodynamic collapse is possible.

For example, if the RV pressure pulse is weak, the signal-to-noise ratio may be poor and the accuracy and reliability of hemodynamic-based algorithms for arrhythmia detection may be limited. Hemodynamic collapse may be difficult to distinguish from normal hemodynamic function if the pulse pressure signal under normal conditions is already weak.

In one embodiment, if an average pulse pressure baseline is less than a predetermined threshold, e.g. if the LT average pulse pressure is less than approximately 20 mmHg, as determined at block 318, the baseline measurements are disqualified for use in arrhythmia detection and therapy delivery decision-making purposes at block 326. Hemodynamic arrhythmia detection algorithms, such as method 200 of FIG. 3, will not be enabled at block 328. Baseline measurements may be repeated at a later time in an attempt to obtain measurements meeting the qualification criteria.

The RV pressure pulse and maximum dP/dt are expected to be higher during sinus tachycardia than during rest. A measurable difference between the LT baseline measurements and the ST baseline measurements thus enables discrimination between sinus tachycardia, supraventricular tachycardias, and true VT/FVT or VF. If a patient is lacking cardiac reserve, i.e. the hemodynamic response during exercise is not significantly different than during rest, LT and ST baseline measurements will not be significantly different. If valid ST baseline measurements are available (i.e., not expired as determined at block 312) the valid ST baselines are compared to the LT baselines at block 320. If the ST baselines are not greater than the LT baseline measurements by at least a predetermined margin of error, as determined at block 320, the ST baseline measurements may be disqualified for use in arrhythmia detection and therapy delivery decisions at block 324. Since the LT baseline measurements were qualified at block 318, the hemodynamic detection algorithm is still enabled at block 328. Only portions of the hemodynamic-based algorithm that rely on the ST baseline measurements will be disabled. In some embodiments, a multiple of the LT baseline measurements may be substituted for the ST baseline measurements when a ST baseline is determined to be invalid or disqualified.

If both the LT and ST baseline measurements meet the qualification criteria at blocks 318 and 320, indicating the pressure signal provides acceptable signal strength and the LT and ST baseline measurements are distinguishable from each other, discrimination between hemodynamic collapse, normal sinus rhythm and sinus tachycardia using hemodynamic analysis is possible. An algorithm relying on hemodynamic analysis for arrhythmia detection and therapy delivery decisions is fully enabled at block 328.

It is contemplated that numerous methods may be used for computing baseline measurements. Various embodiments may use different numbers of data points for computing average, median or other statistical values of hemodynamic measurements over predetermined sampling periods. Likewise numerous artifact rejection and signal quality control measures may be implemented to ensure that baseline hemodynamic measurements are reliable.

Figure 5:
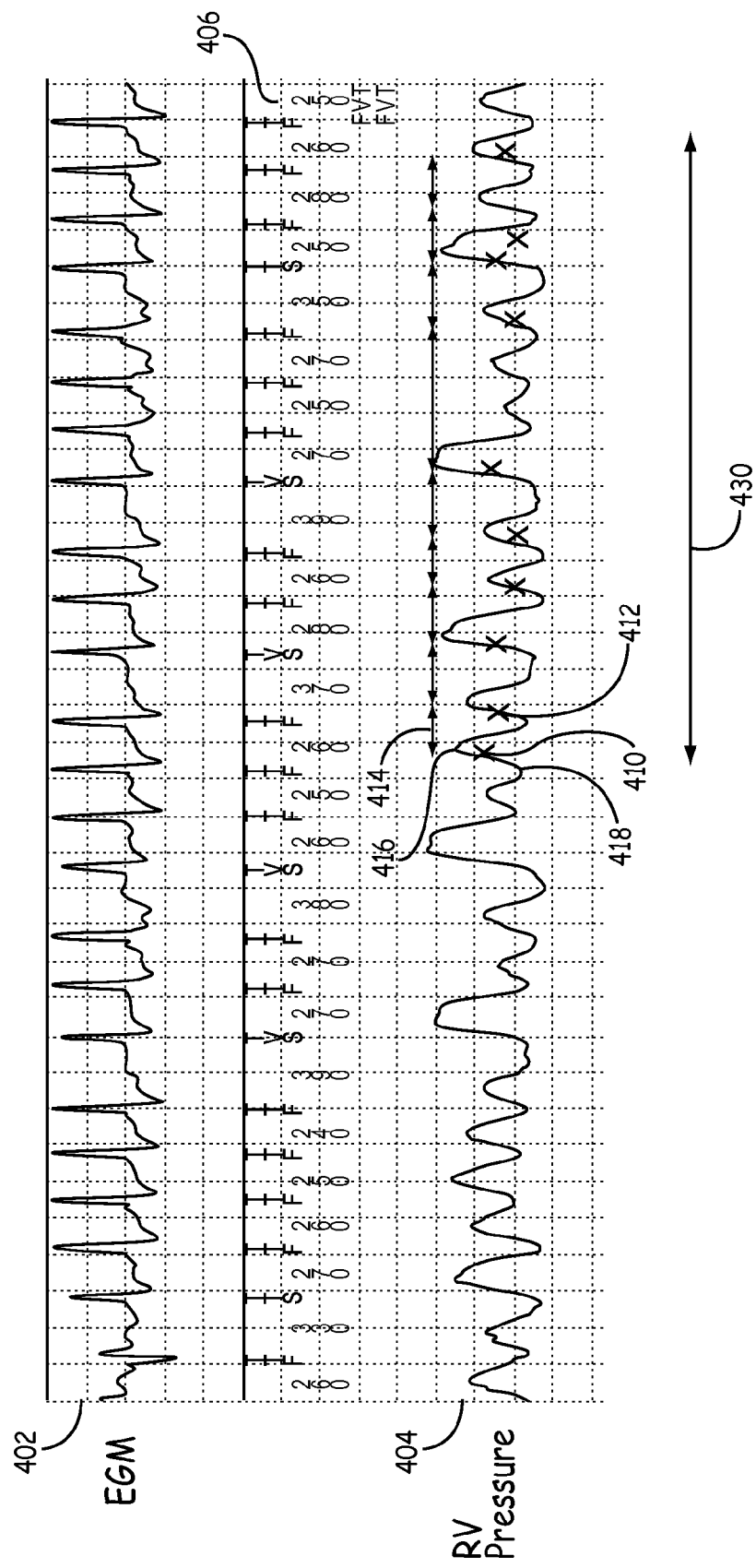
FIG. 5 shows EGM and RV pressure recordings illustrating one method for using mechanical intervals for confirming EGM intervals.

FIG. 5 shows EGM and RV pressure recordings illustrating one method for using mechanical event intervals for confirming EGM event intervals at block 216 of method 200. RR intervals are measured from a ventricular EGM signal 402. In the example shown, a preliminary FVT detection is made at 406 when a fast VT interval counter reaches a programmed NID. Upon making the preliminary arrhythmia detection based on the electrical event intervals, mechanical event intervals are evaluated from the RV pressure signal 404 to confirm the detected electrical rate.

Mechanical event intervals are identified independent of the sensed electrical intervals. In one embodiment, mechanical event intervals 414 are measured for a predetermined time interval 430 immediately prior to the preliminary arrhythmia detection 406. Time interval 430 may be between 2 and 12 seconds, e.g. approximately 3 seconds, or another predetermined interval.

An onset 410 of a mechanical event interval 414 is identified according to a threshold crossing or other criteria applied to the RV pressure signal 404 for separating RV pressure events, i.e. each pressure pulse waveform. In one embodiment, the onset 410 is identified as the first sample point of three consecutive points sampled at a rate of 64 Hz and having a sample-to-sample difference of approximately 2 mmHg that is positive-going. It is recognized that other criteria may be set for the required the number of sample points and point-to-point magnitude difference and such criteria will depend in part on the sampling rate. An onset 410 may be detected only if a previous onset has not been detected for a predetermined time interval or number of preceding sample points. The mechanical event interval 414 is then measured as the time interval between two consecutive mechanical event onsets 410 and 412.

In alternative embodiments, an onset 410 of a mechanical event interval can be identified by filtering the pressure signal or differentiating the signal to obtain a dP/dt waveform. A crossing of a dP/dt threshold by the dP/dt waveform may define onset 410. Using a relatively low dP/dt threshold, e.g. approximately 200 mmHg/s or less, for example approximately 100 mmHg/s, allows even relatively small pressure pulse events to be identified making accurate mechanical event intervals to be reliably measured.

The mechanical event intervals 414 are measured over the analysis time period 430 and an average or median event interval is computed. The average mechanical event interval is then compared to a measure of the electrical event intervals obtained from the EGM signal. For example, the average, median, or other statistical measure of a predetermined number of consecutive RR intervals preceding the preliminary arrhythmia detection 406 may be compared to the average mechanical event interval.

In one embodiment, the average mechanical event interval measured over a 3 second time interval 430 is compared to the second smallest RR interval measured in the eight RR intervals preceding the preliminary arrhythmia detection. If the average mechanical event interval is approximately two times longer than the electrical event interval measurement, there is evidence of T-wave oversensing of the EGM signal. Each cardiac cycle is counted twice on the EGM signal when both the R-wave and T-wave are each sensed on each cardiac cycle, approximately doubling the actual heart rate.

Referring to method 200 of FIG. 3, in one embodiment the electrical event intervals are confirmed as valid arrhythmia detection intervals at block 216 if the mechanical event interval measurement meets a signal quality threshold and is less than approximately 1.8 times the electrical event interval measurement. This confirmation reduces the occurrence of false arrhythmia detection caused by T-wave oversensing. If the mechanical event interval measurement is greater than approximately 1.8 times the electrical event interval measurement, arrhythmia detection is withheld at block 232. The withholding of a preliminary arrhythmia detection made based on EGM intervals results in the withholding of device-delivered arrhythmia therapies. Oversensing of the EGM signal may be causing a high rate to be falsely detected. Method 200 returns to block 206 to acquire more data before confirming an arrhythmia detection. The preliminary detection itself is not in effect cancelled in that additional analysis performed of the EGM signal and/or the hemodynamic signal may result in redetection and/or confirmation of the arrhythmia episode. The effect of withholding a final detection or confirmation of the preliminary detection at block 232 is to withhold therapy delivery to allow more data to be analyzed to confirm the rhythm and select the most appropriate therapy.

Referring again to FIG. 5, the pulse pressure may be determined for a mechanical event as the difference between a maximum pressure 416 and a minimum pressure 418. The maximum pressure 416 is identified as the maximum sample point occurring during the event interval 414. The minimum pressure 418 may be identified as the minimum sample point during a predetermined onset sampling interval, e.g. approximately 100 ms, preceding the onset 410. Alternatively, the minimum pressure may be identified as the minimum sample point during the event interval 414 or during the preceding event interval.

A pulse pressure measurement may be used to verify that the RV pressure signal strength is high enough to allow reliable mechanical event interval measurements. As can be seen in FIG. 5, two pressure pulses are missed due to their very low amplitude. If the average pulse pressure during interval 430 is less than a predetermined minimum signal quality threshold, e.g. less than approximately 20 mmHg, the mechanical event intervals may be rejected for use in verifying the electrical event intervals. Mechanical event interval analysis will not be used to withhold an EGM-based arrhythmia detection.

Similarly, a minimum number of mechanical event intervals identified during the interval 430 may be required before using the mechanical event intervals for verifying electrical event intervals. If the pulse pressure signals are so low that less than a required number of mechanical event intervals are identified, for example less than two intervals, mechanical event interval analysis is not used to withhold the EGM-based arrhythmia detection. In some embodiments, only a single mechanical event interval identified during interval 430 may be required.

The methods shown in FIG. 5 for identifying mechanical event intervals 414 using a detected onset 410 to allow measurement of pulse pressure as the difference between a maximum 414 and minimum 418 on a beat-by-beat basis may also be used during the computation of the LT and ST average baseline measurements described above. A maximum positive dP/dt may also be measured for each mechanical event, for example a maximum positive dP/dt occurring after an identified onset 410. The maximum positive dP/dt values are used for computing LT and ST baseline dP/dt measurements.

In alternative embodiments, sensed electrical events (e.g. R-waves) and paced events may be used as fiducial points for setting a time window in which a mechanical event measurement is taken, such as maximum positive dP/dt or pulse pressure. In one embodiment a measurement window is set upon an EGM sensed or paced event. The occurrence of a mechanical event within that measurement window, or within a separately defined mechanical event window, is verified by identifying a positive slope of the hemodynamic signal followed by a negative slope of the hemodynamic signal. For example, if 3 consecutive 64 Hz sample points have a positive-going difference of at least 2 mmHg, then a pressure pulse upslope is identified. An upslope may alternatively be identified as a positive maximum dP/dt. A pressure pulse downslope is identified by searching, beginning after a maximum signal point following the upslope, for at least two consecutive 64 Hz sample points having a negative-going difference of at least 2 mmHg. When the upslope and downslope points are identified and occur a predetermined time range apart, the occurrence of the pressure pulse is confirmed. Mechanical event measurements, such as dP/dt and pulse pressure may then be identified within the EGM-based measurement time window.

In one embodiment, the upslope and downslope points must be identified within a mechanical event window beginning approximately 100 ms after a sense or paced event and extending until the next sense or paced event or 600 ms, whichever comes first. In addition, in the illustrative embodiment, the upslope and downslope points must be at least approximately 100 ms apart and must not be more than approximately 350 ms apart in order to confirm the mechanical event signal for use in taking event measurements. A mechanical event measurement may then be taken within an EGM-based measurement window or relative to the identified upslope and downslope. For example maximum dP/dt may be measured in a window of 200 ms following a sensed or paced event.

Figure 6:
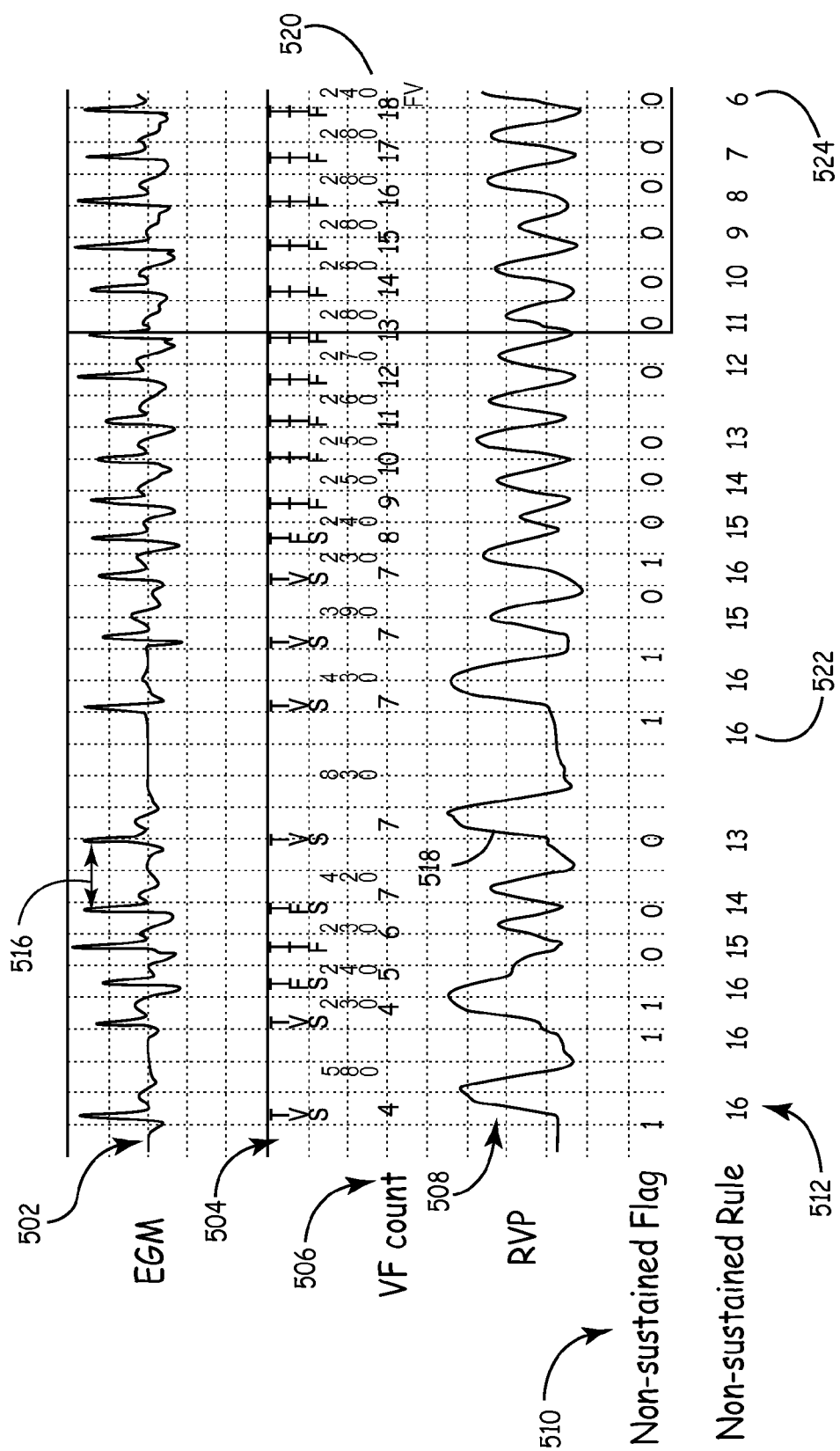
FIG. 6 shows EGM and RV pressure recordings illustrating one method for detecting a non-sustained arrhythmia.

FIG. 6 shows EGM signal 502 and RV pressure signal 508 recordings illustrating one method for detecting a non-sustained arrhythmia at block 218 of method 200 (FIG. 3). Pulse pressure measured in response to a preliminary arrhythmia episode detection can be used for detecting a break in a fast rhythm, i.e. detecting a non-sustained rhythm despite EGM-based NID criteria being satisfied.

A ventricular EGM signal 502 is shown with corresponding annotations 504 indicating the RR interval length in ms and the sensed event label corresponding to the measured RR interval length (VS for ventricular sense intervals longer than the maximum detection interval, FS for fibrillation sense intervals falling into a fibrillation interval range, TF for fast tachycardia sense and so on). A VF counter 506 counts the number of VF and fast VT intervals that are sensed. The VF counter 506 is not increased for ventricular sense (VS) events, which are longer than the programmed arrhythmia detection interval ranges.

When the VF counter 506 reaches a programmed NID, a preliminary VF detection is made at 520. For each long RR interval 516 corresponding to VS events, a corresponding mechanical event 518 is measured to determine if the long RR interval 516 is associated with normal hemodynamic function. Normal or near-normal hemodynamic function associated with a VS event indicates a break in the fast rhythm and is thus evidence of a non-sustained arrhythmia.

Accordingly, when a preliminary arrhythmia detection 520 is made, a preceding number of cardiac cycles are analyzed to determine if any VS events occurred. If a VS event occurs, the hemodynamic signal 508 is analyzed, e.g. pulse pressure is measured, during the RR interval immediately following the VS event to determine if the VS event is associated with normal hemodynamic function.

In one embodiment, this analysis is achieved by implementing a non-sustained arrhythmia flag 510 and a non-sustained rule counter 512. The non-sustained rule counter 512 is initially set to a predetermined number of intervals, for example 16 intervals, whenever the VF counter 506 initially goes from zero to one or reaches another predetermined count less than the NID. In the example shown, the non-sustained rule counter 512 is initialized to 16 when the VF counter 506 reaches 4. The non-sustained rule counter 512 is decreased by one on each ventricular event as long as the non-sustained flag 510 is zero.

If the VF counter 506 is not increased, i.e. if a VS event occurs, the pressure signal is measured during the RR interval immediately following the VS event to determine if good hemodynamic function is present in response to the VS interval 516. For example, the pulse pressure and the maximum dP/dt may be measured for a mechanical event 518 occurring immediately following the VS event. The mechanical event interval 518 associated with a VS event, for purposes of measuring hemodynamic function, may be defined relative to the VS event or based on identifying the mechanical pressure pulse event as described previously wherein the pressure pulse onset is searched for beginning from the VS event. If the pulse pressure and the maximum dP/dt of the pressure pulse 518 are approximately equal to or greater than the LT baseline measurements, the non-sustained flag 510 is set to 1. The non-sustained rule counter 512 is reset to its initial value, as seen at 522 in FIG. 6, in response to the non-sustained flag 510 being set to 1.

The arrhythmia is determined to be a non-sustained arrhythmia. The long electrical event interval resulting in the VS event paired with hemodynamic function equaling or exceeding the LT baseline measurements, or some threshold thereof, indicates a break in the pathological rhythm.

The preliminary VF detection 520 will not be confirmed as VF until the VF counter 506 reaches the NID and the non-sustained rule counter 512 reaches zero. In the example shown, the non-sustained rule counter 512 is at six at 524 when the VF counter 506 reaches the NID at 520 (18 in this example). The preliminary VF detection made in response to the NID being met will not be confirmed until the non-sustained rule counter 512 is zero, or until the hemodynamic analysis timer expires (as described above in conjunction with FIG. 3) and additional EGM analysis confirms the VF detection. If the non-sustained rule counter 512 reaches zero, the VF detection may be confirmed, and a VF therapy delivered as long as the NID requirement is still being met. Thus, an arrhythmia detection may be withheld in response to a single VS event associated with normal hemodynamic function representing a break in the pathological rhythm.

In alternative embodiments, the VF counter 506 may be modified to be reset when the non-sustained flag 510 is high, eliminating the need for a separate non-sustained rule counter 512. The non-sustained flag is high whenever a VS event is immediately followed by a mechanical event measurement that equals or exceeds the LT baseline measurement, or another threshold set to represent normal hemodynamic function corresponding to a break in the arrhythmic rhythm.

Figure 7:
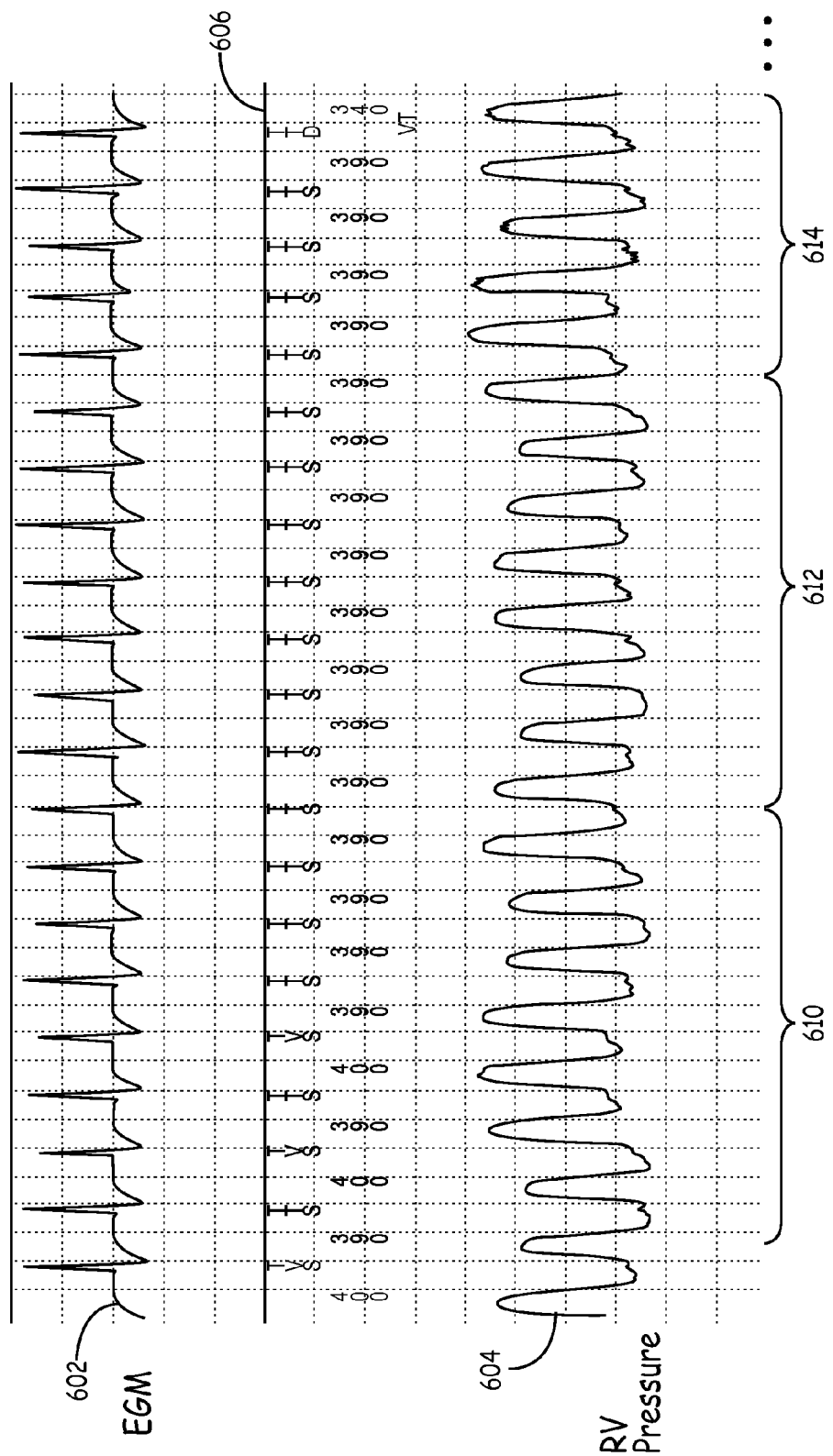
FIG. 7 shows EGM and RV pressure recordings illustrating methods for discriminating sinus tachycardia and supraventricular tachycardia from true VT/FVT or VF using hemodynamic measurements.

FIG. 7 shows EGM signal 602 and RV pressure signal 604 recordings illustrating methods for discriminating sinus tachycardia and supraventricular tachycardia from true VT/FVT or VF using hemodynamic measurements. RR intervals sensed from the EGM signal 602 result in a preliminary arrhythmia detection at 606. In response to the preliminary detection, the RV pressure signal 604 is analyzed to discriminate between true ventricular arrhythmias resulting in hemodynamic collapse needing immediate therapy delivery and sinus tachycardia and SVT.

Upon the preliminary arrhythmia detection 606, the RV pressure signal is evaluated using mechanical event epochs. A mechanical event epoch is defined as a predetermined number of mechanical event intervals, which may or may not be determined independently of the electrical event intervals. An epoch may be set to include eight or more mechanical event intervals. By including at least eight mechanical event intervals, the effects of hemodynamic signal variation due to respiration artifact is expected to be reduced.

However, other embodiments may define a mechanical event epoch to be any desired number of mechanical event intervals or electrical event intervals once the electrical event intervals have been verified to not include oversensing. If the electrical event intervals are verified by independently determined mechanical events, the electrical events may be used to set time windows within which a mechanical event is confirmed and mechanical event measurements are taken, as described previously.

Mechanical event epochs are established when an arrhythmia detection counter reaches a predetermined number. For example, mechanical event epochs may be established when a VT/FVT/VF or combined count counter is increased from 0 to 1 or reaches another predetermined count, e.g., 3.

Alternatively, epochs may be established retrospectively in response to a preliminary arrhythmia detection. Epochs may be established beginning at the time of the preliminary arrhythmia detection, i.e., upon NID criteria being satisfied, and extend earlier in time from the arrhythmia detection time point for a predetermined number of epochs. Accordingly, a hemodynamic signal 604 may be continuously monitored and recorded in memory, e.g. in a looping manner, such that at any given time a minimum duration of the hemodynamic signal is available that would precede a preliminary arrhythmia detection should a detection occur. Alternatively or additionally, epochs may be established from the time of preliminary arrhythmia detection and extend later in time for use in detecting hemodynamic collapse during redetection of the episode.

In FIG. 7, one or more mechanical event epochs 610 through 614 is/are established by identifying groups of consecutive mechanical event intervals beginning when an NID counter reaches a predetermined count. The established epochs may extend up to the time of the preliminary arrhythmia detection 606. Each epoch 610 through 614 includes a predetermined number of mechanical event intervals, for example 8 intervals. An epoch 614 may optionally extend beyond the time of preliminary detection 606 in order to complete the epoch with a required number of mechanical event intervals. Alternatively, epoch 614 may be discarded. In still another embodiment, epoch 614 may be accepted with a fewer number of valid mechanical event intervals.

The onset of each mechanical event interval within an epoch may be identified as described previously in conjunction with FIG. 5 independently from the EGM signal or using electrical events to define windows of time in which to search for a confirmed mechanical event and make mechanical event measurements. Mechanical event measurements are computed from the mechanical events within each established epoch 610 through 614. In the example shown in FIG. 7, the average pulse pressure and the average maximum dP/dt is computed for each epoch 610 through 614. Three different sets of criteria may be applied to the epoch measurements to discriminate between true VT/FVT/VF with hemodynamic collapse, SVT and sinus VT.

In one embodiment, if the average epoch pulse pressure for the most recent 2 epochs (or other predetermined number of epochs) preceding the preliminary arrhythmia detection 606 is less than a predetermined percentage of the LT pulse pressure baseline, hemodynamic collapse is detected. Referring back to FIG. 3, if the mechanical interval measurements confirm the electrical interval measurements at block 216, and no rhythm break is detected at block 218, the detection of hemodynamic collapse at block 220 based on two out of two epochs having a pulse pressure less than approximately 40% (or another predetermined percentage) of the LT baseline results in immediate confirmation of the detected arrhythmia.

In addition or alternatively to the LT baseline comparison, the average pulse pressure or another hemodynamic measure of each epoch may be compared to a predetermined fixed minimum for the detection of hemodynamic collapse. For example, if the average epoch pulse pressure is less than approximately 10 mmHg, and the LT baseline pulse pressure measurement has met the qualification requirement for use in arrhythmia detection, e.g. at least approximately 20 mmHg, hemodynamic collapse is detected.

Upon detecting hemodynamic collapse, immediate delivery of a programmed menu of tiered therapies is initiated. Alternatively, an override of the programmed menu of tiered therapies may be made in response to the hemodynamic collapse to allow immediate progression to a more aggressive shock therapy to treat the potentially lethal arrhythmia.

If two of the three most recent epochs 610 through 614 (or other predetermined n out of m epochs) have an average pulse pressure and average maximum dP/dt greater than or equal to the ST baseline measurements, then the preliminary arrhythmia detection is withheld. When the ST baseline measurements are not qualified or valid, or in addition to the ST baseline requirement, a multiple of the LT baseline measurement may be compared to the epoch pulse pressure and dP/dt measurement to allow sinus tachycardia discrimination. These criteria may be applied at block 222 of method 200 for detecting hemodynamic evidence of sinus tachycardia. Specifically, increased pulse pressure and maximum dP/dt reaching or exceeding the ST baseline measurements, and/or a multiple of the LT baseline measurements, is evidence of sinus tachycardia. Method 200 would advance from block 222 to block 232. No therapies will be delivered until the arrhythmia detection is confirmed using additional EGM and hemodynamic data.

If the fast ventricular rate is the result of a conducted supraventricular tachycardia, sufficient autonomic tone is required to conduct the fast rate from the atrial chambers to the ventricular chambers. This autonomic condition is likely to be reflected in an increased pulse pressure and increased maximum dP/dt. As such, if n out of m, e.g., two out of two (or any other predefined n out of m epochs), selected from the most recent epochs 610 through 614 preceding the preliminary arrhythmia detection 606 have an average pulse pressure and average maximum dP/dt greater than or equal to the LT baseline measurements, and if the measured RR intervals show evidence of cycle length instability, evidence of supraventricular tachycardia is detected at block 224 of method 200 (FIG. 3).

A variety of methods may be used for detecting cycle length instability. For example, if two consecutive RR intervals vary by more than a predetermined amount, cycle length instability may be detected. Hemodynamic measurements may be made on the longer of the two intervals to detect a pulse pressure and maximum dP/dt equaling or exceeding the LT baseline measurements as further evidence of an unstable cycle length associated with SVT.

In evaluating hemodynamics for discrimination of SVT, sinus tachycardia and true ventricular arrhythmias, a variable number of mechanical event epochs may be available depending on the time from starting the establishment of the event epochs until the preliminary arrhythmia detection. For example, only one epoch may be available in which case that one epoch is used to test discrimination criteria. Additionally, some epochs may be discarded because of low hemodynamic signal strength, high artifact, or other signal quality requirements are not met. Alternatively, epochs not meeting signal quality requirement may still be used and counted against meeting the n out of m epochs required to meet hemodynamic requirements for withholding an arrhythmia detection and/or detecting hemodynamic collapse. It is recognized that the specific thresholds of n out of m epochs meeting various hemodynamic criteria may vary between embodiments and may be programmable parameters.

Figure 8:
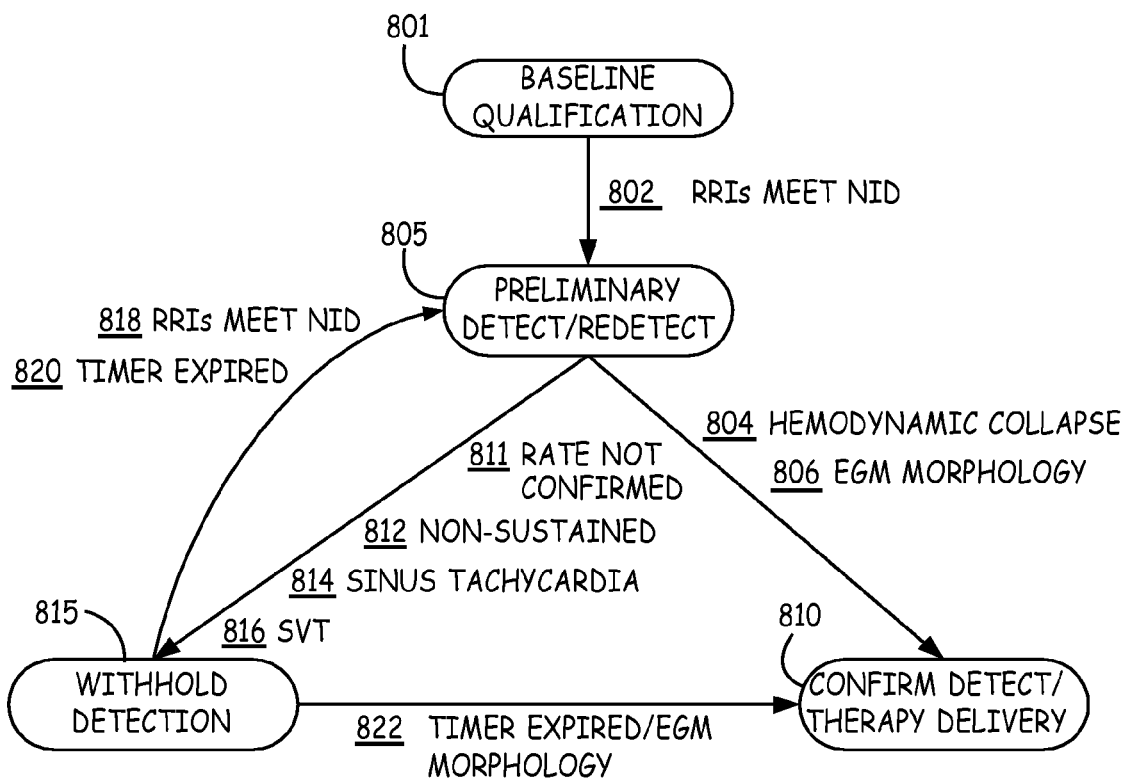
FIG. 8 is a state diagram illustrating transitions between a preliminary detection state, a confirmed detection state and a withhold detection state during operation of an ICD.

FIG. 8 is a state diagram illustrating the transitions between a preliminary detection state 805, a confirm detection state 810 and a withhold detection state 815. Initially, LT and ST baseline measurements are obtained and qualified at state 801. An arrhythmia detection and therapy delivery decision algorithm is then enabled. The preliminary detection state 805 is initially entered whenever electrical event intervals meet NID criteria 802. The preliminary detection state 805 moves to the confirm detection state 810 in response to a hemodynamic collapse rule 804 being satisfied or an EGM morphology analysis rule 806 being satisfied and thus confirming the detected arrhythmia.

In one embodiment the hemodynamic collapse rule 804 requires:
 a) RR intervals meet NID criteria,
 b) mechanical event intervals confirm electrical event intervals, c) rhythm is sustained (no break detected), and d) hemodynamic collapse detected (e.g., n out of m most recent epochs have average pulse pressure less than a percentage of the LT pulse pressure).

Therapy is delivered in the confirm detection state 810 according to a programmed menu of therapies or according to a menu override response to the detected hemodynamic collapse.

Transition from preliminary detection state 805 directly to confirm detection state 810 may also occur when EGM morphology analysis 806 is performed in response to no hemodynamic collapse being detected and no hemodynamic evidence of sinus tachycardia or SVT being detected. In other words, the hemodynamic analysis may fall into a "gray area" in which none of the hemodynamic discrimination rules are met (relating to detecting hemodynamic collapse, sinus tachycardia, or SVT). When the hemodynamic measures do not meet rules for withholding the arrhythmia detection, i.e. sinus tachycardia or SVT rules are not met (as described further below), and hemodynamic collapse is not detected to confirm the arrhythmia, the EGM morphology analysis is performed in an attempt to confirm the preliminary detection. The EGM morphology rule 806 requires all of the following criteria to be met in one embodiment:

a) RR intervals meet NID criteria, b) mechanical event intervals confirm electrical event intervals, c) rhythm is sustained (no break detected), d) sinus tachycardia and SVT rules not met (and no hemodynamic collapse), and e) EGM morphology analysis results in confirmed arrhythmia morphology detection.

The preliminary detection state 805 transitions to a withhold detection state 815 in response to any of the following rules: rate not confirmed 811, non-sustained arrhythmia 812, sinus tachycardia evidence 814, or SVT evidence 816 being met. Though not explicitly shown in FIG. 8, an additional EGM morphology based rule may cause transition from state 805 to withhold detection state 815. In particular, when none of the rules 811 through 816 are satisfied, and hemodynamic collapse is not detected, EGM morphology analysis may cause the arrhythmia detection to be withheld.

In one embodiment, the rate not confirmed rule 811 requires:

a) average pulse pressure greater than or equal to the LT baseline pulse pressure b) average pulse pressure greater than or equal to a predetermined minimum signal strength threshold (e.g., 20 mmHg), and c) mechanical event interval length greater than approximately 1.8 times the electrical event interval length.

When the rate not confirmed rule 811 is satisfied, T-wave oversensing may be occurring. Additional EGM signal monitoring is performed.

The non-sustained arrhythmia rule 812 requires:

a) a VS event occurring when the VF count is greater than zero, b) a pulse pressure immediately following the VS event is greater than or equal to the LT baseline pulse pressure, c) a pulse pressure immediately following the VS event is greater than or equal to a minimum signal strength threshold, and d) a maximum dP/dt immediately following the VS event is greater than or equal to the LT baseline dP/dt.

If the non-sustained arrhythmia rule 812 is satisfied, a break in the fast rhythm associated with good hemodynamic function is present. The arrhythmia detection is withheld.

The sinus tachycardia rule 814 requires:

a) n out of m mechanical event epochs have an average pulse pressure greater than the minimum signal strength threshold, b) n out of m epochs have an average pulse pressure greater than or equal to the ST baseline pulse pressure and greater than or equal to a multiple of the LT baseline pulse pressure (or only a multiple of the LT baseline pulse pressure if valid ST baseline is not available), and c) n out of m epochs have an average dP/dt greater than or equal to the ST baseline dP/dt and greater than or equal to a multiple of the LT baseline dP/dt (or only a multiple of the LT baseline dP/dt if valid ST baseline is not available).

When the sinus tachycardia evidence rule 814 fires, evidence of sinus tachycardia based on increased hemodynamic function causes the arrhythmia detection to be withheld.

The SVT rule 816 requires:

a) RR interval instability criteria met, b) a longer RR interval consecutively following a shorter RR interval having a pulse pressure greater than or equal to a minimum signal strength threshold and greater than or equal to the LT baseline pulse pressure, c) the longer RR interval consecutively following the shorter RR interval having a maximum dP/dt greater than or equal to the LT baseline dP/dt, d) n out of n epochs have an average pulse pressure greater than or equal to minimum signal strength threshold and greater than or equal to the LT baseline pulse pressure, and e) n out of n epochs have an average maximum dP/dt greater than or equal to the LT baseline pulse pressure.

When the SVT rule 816 fires, evidence of RR interval instability and normal hemodynamic function suggests the fast ventricular rate detected using the EGM signal is caused by an SVT. Accordingly, the arrhythmia detection is withheld in state 815.

The withhold detection state 815 transitions back to the preliminary detect/redetect state 805 when RR intervals meet NID redetection criteria 818. The withhold detection state 815 may also transition back to state 805 if a hemodynamic analysis timer expires 820 and EGM morphology analysis performed in response to timer expiration does not confirm the rate-based detection.

Upon returning to state 805 in a redetection condition, some of the hemodynamic rules may be disabled for the remainder of the detected episode. For example, once the mechanical event intervals confirm the electrical event intervals in response to a preliminary arrhythmia detection, the mechanical event interval rule may be disabled thereafter such that mechanical event intervals cannot later fail to confirm the electrical event intervals during the same preliminarily detected/redetected episode. In another embodiment, the hemodynamic collapse rule and/or its associated therapy sequencing may only be applied during a redetection not following a preliminary detection. Alternatively or additionally, the hemodynamic collapse rule may be applied only when the preliminary detection/redetection is FVT or VF, not VT.

The withhold detection state 815 may transition to the confirm detection state 810 if EGM morphology analysis 822, performed in response to expiration of a hemodynamic timer, confirms the arrhythmia detection. Therapy is delivered according to a programmed menu of therapies.

Thus, an implantable medical device and associated methods for arrhythmia detection and therapy delivery decisions have been presented in the foregoing description with reference to specific embodiments. It is appreciated that various modifications to the referenced embodiments may be made without departing from the scope of the invention as set forth in the following claims.

We claim:

1. A method of detecting an arrhythmia in a medical device, comprising:
   sensing cardiac electrical signals;
   sensing cardiac hemodynamic signals;
   determining a long-term baseline hemodynamic measurement in response to a plurality of the sensed cardiac hemodynaic signals;
   detecting a period of increased metabolic demand in response to the sensed cardiac electrical signals;
   determining a sinus tachycardia baseline hemodynamic measurement in response sensing of cardiac hemodynamic signals during the detected period of increased metabolic demand; and
   detecting the arrhythmia and delivering therapy in response to one of only the sensed cardiac electrical signals and the sensed cardiac electrical signals in combination with one or both of the determined long-term baseline hemodynamic measurement and the sinus tachycardia baseline hemodynamic measurement.

2. The method of claim 1, wherein determining a period of increased metabolic demand comprises detecting a rate corresponding to the sensed cardiac electrical signal greater than a cardiac resting rate and less than a tachycardia detection rate.

3. The method of claim 2, wherein the long-term baseline hemodynamic measurement is determined over at least approximately a 24 hour period and the sinus tachycardia baseline measurement is determined over at least approximately a 30 second period of detected increased metabolic demand.

4. The method of claim 1, further comprising determining whether the long-term baseline hemodynamic measurement and the sinus tachycardia baseline hemodynamic measurement are reliable.

5. The method of claim 4, wherein determining whether the long-term baseline hemodynamic measurement and the sinus tachycardia baseline hemodynamic measurement are reliable comprises determining whether the long-term baseline hemodynamic measurement is less than a predetermined threshold, and wherein detecting the arrhythmia and delivering therapy comprises:
   detecting the arrhythmia and delivering therapy in response to the sensed cardiac signals and one or both of the determined long-term baseline hemodynamic measurement and the determined sinus tachycardia baseline hemodynamic measurement in response to the long-term baseline hemodynamic measurement not being less than the predetermined threshold; and
   detecting the arrhythmia and delivering therapy in response to only the sensed cardiac signals in response to the long-term baseline hemodynamic measurement being less than the predetermined threshold.

6. The method of claim 5, wherein the hemodynamic signal corresponds to a pressure signal and the predetermined threshold corresponds to approximately 20 mmHG.

7. The method of claim 5, wherein determining whether the long-term baseline hemodynamic measurement and the sinus tachycardia baseline hemodynamic measurement are reliable further comprises determining whether the determined sinus tachycardia baseline hemodynamic measurement is greater than the determined long-term baseline hemodynamic measurement, and wherein detecting the arrhythmia and delivering therapy further comprises:
   detecting the arrhythmia and delivering therapy in response to the sensed cardiac signals and both the determined long-term baseline hemodynamic measurement and the determined sinus tachycardia baseline hemodynamic measurement in response to the long-term baseline hemodynamic measurement not being less than the predetermined threshold and the determined sinus tachycardia baseline hemodynamic measurement being greater than the determined long-term baseline hemodynamic measurement; and
   detecting the arrhythmia and delivering therapy in response to only the sensed cardiac signals and the determined long-term baseline hemodynamic measurement in response to the long-term baseline hemodynamic measurement not being less than the predetermined threshold and the determined sinus tachycardia baseline hemodynamic measurement not being greater than the determined long-term baseline hemodynamic measurement.

8. The method of claim 7, further comprising determining the sinus tachycardia baseline hemodynamic measurement as a multiple of the determined long-term baseline hemodynamic measurement in response to the determined sinus tachycardia baseline hemodynamic measurement not being greater than the determined long-term baseline hemodynamic measurement.

9. The method of claim 1, further comprising:
   detecting an episode of cardiac electrical event intervals meeting cardiac arrhythmia detection criteria in response to the sensed cardiac electrical signals;
   detecting a cardiac electrical event interval of the detected episode as a long interval not meeting an arrhythmia interval criteria;
   sensing a hemodynamic signal in response to detecting one of the cardiac electrical event intervals of the detected episode as a long interval not meeting an arrhythmia interval criteria;
   identifying the detected episode as non-sustained in response to a first cardiac mechanical event measurement from the hemodynamic signal immediately following the long interval not being less than the determined long-term baseline hemodynamic measurement; and
   withholding therapy in response to the determined non-sustained detected episode.

10. The method of claim 1, further comprising:
    detecting an episode of cardiac electrical event intervals meeting cardiac arrhythmia detection criteria in response to the sensed cardiac electrical signals;
    identifying, in response to the sensed hemodynamic signals, a plurality of mechanical event intervals during the detected episode;
    computing a mechanical event interval measurement from the plurality of mechanical event intervals;
    computing from the electrical signal an electrical event interval measurement during the episode;
    comparing the mechanical event interval measurement to the electrical event interval measurement; and
    withholding the cardiac arrhythmia detection of the episode in response to the comparing.

11. The method of claim 10, wherein the cardiac arrhythmia detection is withheld if the mechanical event interval measurement is greater than approximately 1.8 times the electrical event interval measurement.

12. A medical device for detecting an arrhythmia, the device comprising:

a plurality of sensors sensing cardiac electrical signals and cardiac hemodynamic signals;
a therapy delivery module to deliver therapy; and
a microprocessor, coupled to the plurality of sensors and the therapy delivery module, the microprocessor configured to determine a long-term baseline hemodynamic measurement in response to a plurality of the sensed cardiac hemodynaic signals, detect a period of increased metabolic demand in response to the sensed cardiac electrical signals, determine a sinus tachycardia baseline hemodynamic measurement in response sensing of cardiac hemododynamic signals during the detected period of increased metabolic demand, and detect the arrhythmia and control the therapy delivery module to deliver therapy in response to one of only the sensed cardiac electrical signals and the sensed cardiac electrical signals in combination with one or both of the determined long-term baseline hemodynamic measurement and the sinus tachycardia baseline hemodynamic measurement.

13. The device of claim 12, wherein the detected period of increased metabolic demand corresponds to a rate of the sensed cardiac electrical signal greater than a cardiac resting rate and less than a tachycardia detection rate.

14. The device of claim 13, wherein the long-term baseline hemodynamic measurement is determined over at least approximately a 24 hour period and the sinus tachycardia baseline measurement is determined over at least approximately a 30 second period of detected increased metabolic demand.

15. The device of claim 12, wherein the microprocessor determines whether the long-term baseline hemodynamic measurement and the sinus tachycardia baseline hemodynamic measurement are reliable.

16. The device of claim 15, wherein the microprocessor detects the arrhythmia in response to the sensed cardiac signals and one or both of the determined long-term baseline hemodynamic measurement and the determined sinus tachycardia baseline hemodynamic measurement in response to the long-term baseline hemodynamic measurement not being less than a predetermined threshold, and detects the arrhythmia in response to only the sensed cardiac signals in response to the long-term baseline hemodynamic measurement being less than the predetermined threshold.

17. The device of claim 16, wherein the hemodynamic signal corresponds to a pressure signal and the predetermined threshold corresponds to approximately 20 mmHG.

18. The device of claim 16, wherein the microprocessor detects the arrhythmia in response to the sensed cardiac signals and both the determined long-term baseline hemodynamic measurement and the determined sinus tachycardia baseline hemodynamic measurement in response to the long-term baseline hemodynamic measurement not being less than the predetermined threshold and the determined sinus tachycardia baseline hemodynamic measurement being greater than the determined long-term baseline hemodynamic measurement, and detects the arrhythmia in response to only the sensed cardiac signals and the determined long-term baseline hemodynamic measurement in response to the long-term baseline hemodynamic measurement not being less than the predetermined threshold and the determined sinus tachycardia baseline hemodynamic measurement not being greater than the determined long-term baseline hemodynamic measurement.

19. The device of claim 18, wherein the microprocessor determines the sinus tachycardia baseline hemodynamic measurement as a multiple of the determined long-term baseline hemodynamic measurement in response to the determined sinus tachycardia baseline hemodynamic measurement not being greater than the determined long-term baseline hemodynamic measurement.

20. The device of claim 12, wherein the microprocessor is further configured to detect an episode of cardiac electrical event intervals meeting cardiac arrhythmia detection criteria in response to the sensed cardiac electrical signals, detect a cardiac electrical event interval of the detected episode as a long interval not meeting an arrhythmia interval criteria, identify the detected episode as non-sustained in response to a first cardiac mechanical event measurement from the hemodynamic signal sensed immediately following the detected long interval not being less than the determined long-term baseline hemodynamic measurement, and withhold delivery of therapy by the therapy delivery module in response to the determined non-sustained detected episode.

21. The device of claim 12, wherein the microprocessor is further configured to detect an episode of cardiac electrical event intervals meeting cardiac arrhythmia detection criteria in response to the sensed cardiac electrical signals, identify, in response to the sensed hemodynamic signals, a plurality of mechanical event intervals during the detected episode, determine a mechanical event interval measurement from the plurality of mechanical event intervals, determine, in response to the electrical signal, an electrical event interval measurement during the episode, compare the mechanical event interval measurement to the electrical event interval measurement, and withhold the cardiac arrhythmia detection of the episode in response to the comparing.

22. The device of claim 21, wherein the cardiac arrhythmia detection is withheld if the mechanical event interval measurement is greater than approximately 1.8 times the electrical event interval measurement.

* * * * *